(12) United States Patent
Wang et al.

(10) Patent No.: US 8,053,227 B2
(45) Date of Patent: Nov. 8, 2011

(54) BIOSENSOR (75) Inventors: Cheng Wang, Taoyuan Hsien (TW);
Ya-Ping Xie, Taoyuan Hsien (TW);
Yu-Qin Tang, Taoyuan Hsien (TW)

(73) Assignee: Delta Electronics, Inc., Taoyuan Hsien (TW)

( * ) Notice: Subject to any disclaimer, the term of this patent is extended or adjusted under 35 U.S.C. 154(b) by 588 days.

(21) Appl. No.: 12/143,455

(22) Filed: Jun. 20, 2008

(65) Prior Publication Data
US 2009/0244540 A1 Oct. 1, 2009

(30) Foreign Application Priority Data
Mar. 28, 2008 (TW) .............................. 97111249 A (51) Int. Cl.
*G01N 33/551* (2006.01)
*G01N 33/552* (2006.01)

(52) U.S. Cl. ............... 435/287.2; 422/82.05; 422/82.11; 435/6.1; 435/288.7; 436/164; 436/524; 436/525; 436/527

(58) Field of Classification Search .................... None
See application file for complete search history.

(56) References Cited

U.S. PATENT DOCUMENTS
4,844,613 A * 7/1989 Batchelder et al. ........... 356/318
5,591,407 A * 1/1997 Groger et al. ............. 422/82.05
5,991,048 A 11/1999 Karlson et al.

* cited by examiner

*Primary Examiner* — Chris L Chin
(74) *Attorney, Agent, or Firm* — Muncy, Geissler, Olds & Lowe, PLLC (57) ABSTRACT A biosensor provided herein includes a semiconductor laser device having an optical resonator with at least one reflective surface and a light output surface, and a surface plasmon resonance (SPR) unit disposed on the reflective surface of the optical resonator. The SPR unit has specific biological molecules fixed thereon for reacting with corresponding biological molecules of an analyzed object.

19 Claims, 6 Drawing Sheets

BIOSENSOR

CROSS REFERENCE TO RELATED APPLICATIONS

This Non-provisional application claims priority under 35 U.S.C. §119(a) on Patent Application No(s). 097111249 filed in Taiwan, Republic of China on Mar. 28, 2008, the entirety of which is incorporated by reference herein.

BACKGROUND OF THE INVENTION

1. Field of the Invention

The present invention relates to a biosensor, and in particular, to a surface plasmon resonance sensor including a semiconductor laser device for performing resonance amplification, to thereby proceed with optical amplification of a minor biological detection signal and for the convenience of signal detection.

2. Description of the Related Art

Due to specificity of a biosensor, a predetermined enzyme or reactants against predetermined analytes for reacting therewith are needed and are provided within a sample and the biosensor of various types can be thus designed according to electrical, optical, and mass differences before and after a bio-reaction. Due to the relative weak interaction between biomolecules, useful signals may possibly immerge by an interference signal due to the poor processing of weak signals. A common detection method used in a biosensor is to detect biological reaction signals by surface plasmon resonance (SPR) effects.

The surface plasmon resonance (SPR) detection method is basically achieved by total reflection of light on a surface of the metal film, thereby causing evanescent waves within the metal film. Additionally, a reflected light intensity is detected with a tremendous decrease while resonance occurs between the evanescent wave and the surface plasmon. For the SPR detector, the detection intensity is typically improved by changing surfaces of the metal films and structures of the detected surface. As described in U.S. Pat. No. 5,991,048, an inter-electrical media layer is used as a way to improve sensitivity of the metal film and the detecting surface. However, the SPR techniques use only detection of a single or multiple reflection of light and the detected signals are not effectively amplified.

BRIEF SUMMARY OF THE INVENTION

Therefore, it is an object of the present invention to provide a biosensor to perform optical amplification of weak bio-reaction signals, thereby simplifying signal processing of the detection circuits.

An exemplary biosensor provided herein includes a semiconductor laser device including an optical resonator with at least one reflective surface and a light output surface, and a surface plasmon resonance (SPR) unit disposed on the at least one reflective surface of the optical resonator.

In the embodiment, the optical resonator provides photons to travel back and forth therein, thus dramatically amplifying the photon signal due to the stimulated emission, when gain of the photons is greater than consumption thereof (i.e. injection currents are greater than threshold currents).

The function of the SPR unit is to generate surface plasmon resonance (SPR) effects and the SPR unit can be a thin metal film of high reflectivity. Most of the photon energy is totally reflected back to the optical resonator while the photon radiates the SPR unit and part of the photon energy is absorbed by the SPR unit in the evanescent wave form. When the specific biological molecules bound on the SPR unit react with an analyzed object, variation of the photon energy of the evanescent wave occurs, thereby allowing the photon energy reflected by the SPR unit to be adjusted by the biological molecule reaction signal on the SPR unit, thus resulting in the outputted laser intensity signal to vary along with the variation of the biological molecule reaction signals.

The biosensor of the present invention utilizes multiple amplification characteristics of a semiconductor laser device, wherein the photon energy in the optical resonator is adjusted by surface plasmon resonance of the reflective surface of the optical resonator while moving back and forth once therein. The photon energy is correspondingly adjusted by the biological molecule reaction signal over the surface of the SPR unit. Following multiple photon travels, the biological molecule reaction signal on the surface of the SPR unit is thus effectively amplified, thereby allowing a weak biological reaction signal to be easily detected, thus simplifying the detection method of the biosensor.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

First Embodiment

Figure 1A:
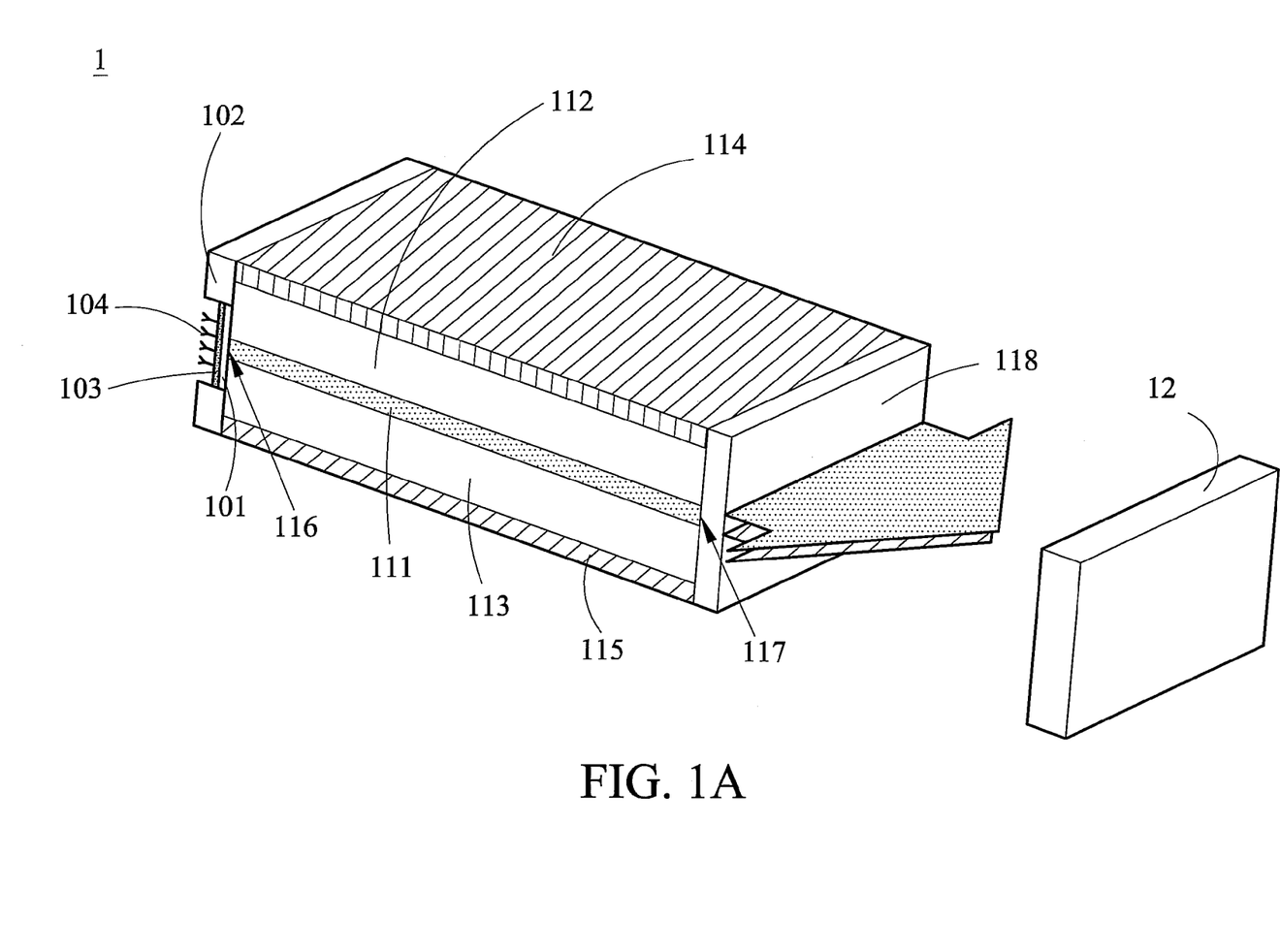
FIG. 1A and FIG. 1B are stereo and cross-sectional diagrams of a biosensor in accordance with a first embodiment of the invention, respectively.
Figure 1B:
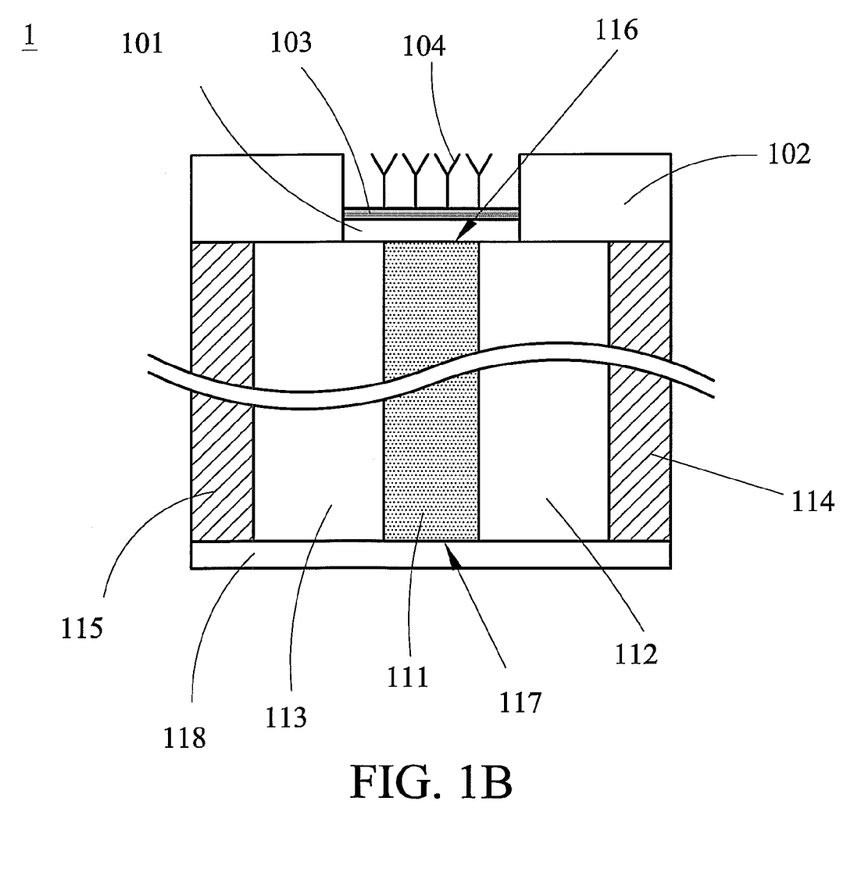

FIGS. 1A and 1B are stereo and cross-sectional diagrams showing a biosensor in accordance with a first embodiment of the invention, respectively. The biosensor 1 includes a surface plasmon resonance (SPR) unit 101 and a semiconductor laser device.

The semiconductor laser device includes an optical resonator including a reflective surface 116 and a light output surface 117, thereby providing photons to move back and forth within the optical resonator. Due to stimulated emission, the photon signal is thus dramatically amplified and energy of the photon is then transmitted in a laser form when gain of the photons is greater than consumption thereof (i.e. the injection current greater than the threshold current). The semiconductor laser device in this embodiment can be, for example, a Fabry Perot (FP) semiconductor laser device, but is not limited thereto. The optical resonator of the FP semiconductor laser device is a Fabry Perot (FP) cavity.

The SPR unit 101 is disposed on a reflective surface 116 of the optical resonator. The SPR unit 101 is for generating surface plasmon resonance (SPR) effect. The SPR unit 101 can be a thin metal film of high reflectivity, such as Au, Ag, Cu or a composite multi-layer thereof. The SPR unit 101 can also be a semiconductor layer or a dielectric layer composed of metal oxides, but is not limited thereto. A binding layer 103 is further provided on the SPR unit 101 to fix the specific biological molecules 104. The specific biological molecules 104 mainly include DNA segments, antigen, antibody, enzyme, co-enzyme and other bio-molecules for reacting with corresponding biological molecules of the analyzed object.

The semiconductor laser device mainly includes an active layer 111, a P-type carrier confinement layer 112, an N-type carrier confinement layer 113, a P-type electrode layer 114, and an N-type electrode 115. The reflective surface 116 and the light output surface 117 of the active layer 111 of the semiconductor laser device restrict photon to move back and forth within the active layer 111. The active layer 111 may include P-type GaAs semiconductor material. The P-type carrier confinement layer 112 is disposed on one side of the active layer 111 and may include P-type $Al_xGa_{1-x}As$ semiconductor material. The N-type carrier confinement layer 113 is disposed on the other side of the active layer 111 and may include N-type $Al_xGa_{1-x}As$ semiconductor material. Thus, dual heterostructure is formed on both sides of the active layer 111. The P-type electrode 114 is disposed on the P-type carrier confinement layer 112 and materials thereof can be, for example, Ni/Cu alloy, but is not limited thereto. The N-type electrode 115 is disposed on the N-type carrier confinement layer 113 and the material thereof can be, for example, Ti/Al/Au alloy, but is not limited thereto. An electric field can be applied through the N-type electrode 115 and the P-type electrode, thereby injecting carriers to the active layer 111 and achieving population inversion distribution. At least one cleavage end surface of the active layer 111 is the reflective surface 116, the other cleavage end surface of the active layer 111 is the light output surface 117 to thereby form the optical resonator. During back and forth travel of the photon in the optical resonator, stimulated emission is thus generated and thereby amplifies a light signal thereof.

In addition, the biosensor 1 further includes an isolation region 102 disposed on the reflective surface 116 of the semiconductor laser device and on both sides of the SPR unit 101 to thereby prevent the SPR unit 101 from connecting to the N-type electrode 115 and P-type electrode 114 of the semiconductor laser device 114. A trench is also formed above the surface of the SPR unit 101, thereby allowing reaction between the bound specific biological molecules 104 with an analyzed object. The isolation regions 102 can be formed of insulating material.

The light output surface 117 of the active layer 111 of the semiconductor laser device is coated with a first dielectric layer 118. The first dielectric layer 118 allows partial reflection and transmission of the laser. The reflection rate of the first dielectric layer 118 depends on the output power of the laser. The first dielectric layer 118 can be alternately stacked dielectric films selected from the group consisting of $SiO_2$, $TiO_2$, ZnS and $MgF_2$. The materials and thickness of the first dielectric layer 118 may vary with different wavelengths of the photon. In a preferred embodiment of the invention, the SPR unit 101 is a metal film having a very high reflectivity against a predetermined wavelength laser such that no additional reflective layer is needed to be formed on the reflective surface 116 and only the first dielectric layer 117 which allows partial reflection is formed on the light output surface 117. If the SPR unit does not have enough reflectivity to a predetermined laser, a second dielectric layer (not shown) is needed and is coated before forming the SPR unit 101. The second dielectric layer (not shown) may be formed by alternately stacked dielectric films selected from the group consisting of $SiO_2$, $TiO_2$, ZnS and $MgF_2$. The materials and thickness of the second dielectric layer may vary with the wavelength of the photons.

The biosensor 1 further includes a detecting unit 12 disposed along a light output direction of the laser. The detecting unit 12 includes a light intensity detection unit and the detected results can be outputted with either a current form or a voltage form.

Second Embodiment

Figure 2:
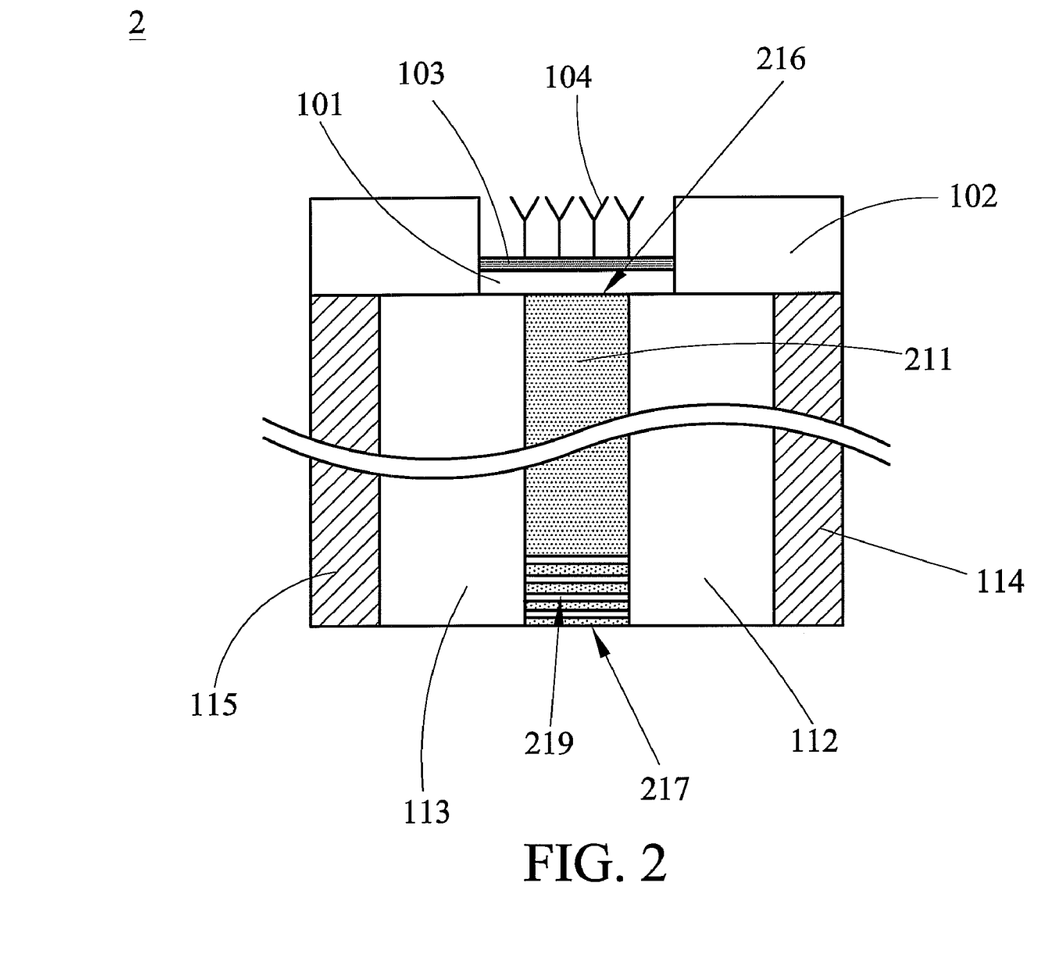
FIG. 2 is a cross-sectional diagram of a biosensor in accordance with a second embodiment of the invention.

FIG. 2 is a cross-sectional view showing a biosensor in accordance with a second embodiment of the invention. The same elements of the biosensor 2 and the biosensor 1 are not described here, for simplicity. The difference between the biosensors 2 and 1 is that the semiconductor laser device in the biosensor 2 herein is a distributed feedback (DFB) laser using a Brag grating 219 for forming a light output surface 217. The films of the Brag grating 219 can be formed with different number of layers according to different wavelength of the photons to thereby provide different reflectivity. The light output surface 217 is formed with the Brag grating 219 at an end of the active layer 211 corresponding to the reflective surface 216, thus providing a half-reflective layer function (with partial reflective function), so that no dielectric layer is needed to be coated over the light output surface 217. In this embodiment, the reflective layer 216 is formed by directly forming the SPR unit 101 thereon without Brag grating.

Third Embodiment

Figure 3:
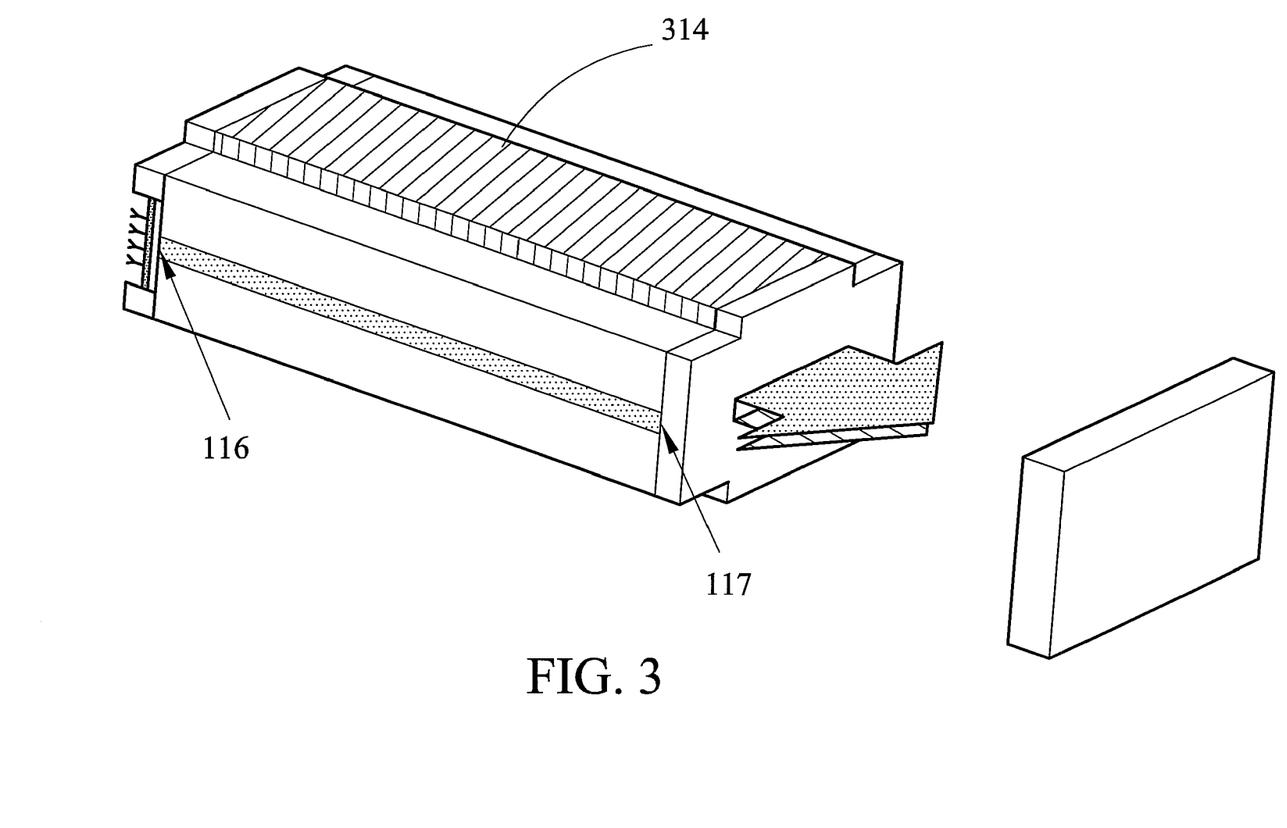
FIG. 3 is a stereo diagram of a biosensor in accordance with a third embodiment of the invention.

FIG. 3 is a schematic view showing a biosensor in accordance with a third embodiment of the invention. The same elements of the biosensor 3 and the biosensors 1 and 2 are not described here, for simplicity. To reduce operating currents, the biosensor 3 is formed with an N-type electrode (not shown) and a P-type electrode 314 with narrow strip structures which extend from the reflective surface 116 to the light output surface 117. This structure also restricts light-emitting area of the laser. The semiconductor laser device shown in FIG. 3 is illustrated as an FP semiconductor laser device and can be, for example, the DFB laser.

Fourth Embodiment

Figure 4:
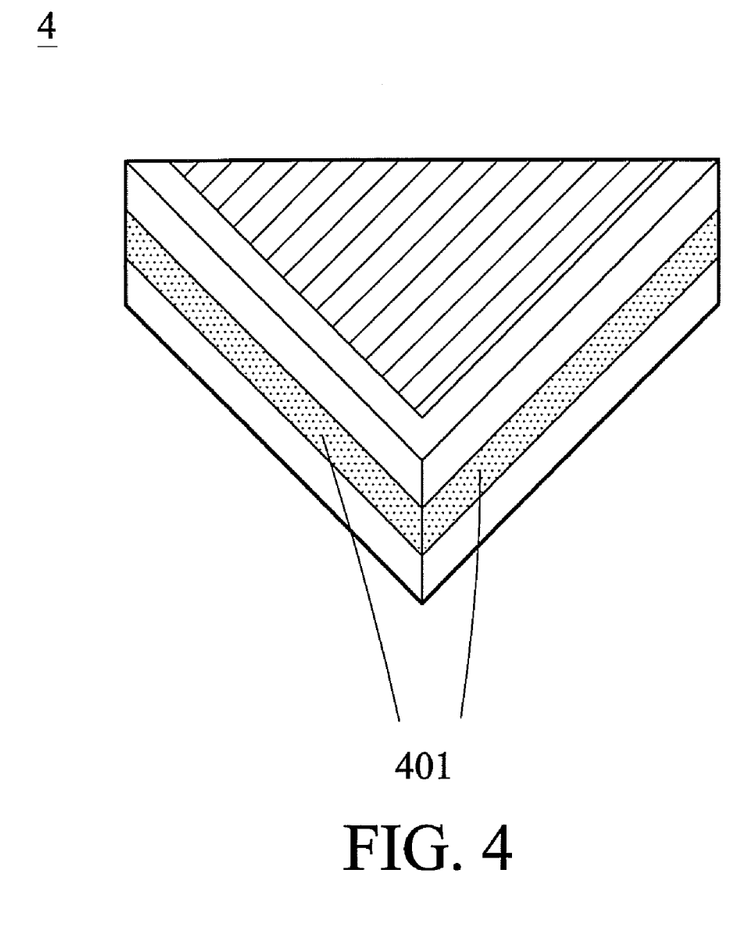
FIG. 4 is a stereo diagram of a biosensor in accordance with a fourth embodiment of the invention.

FIG. 4 is a schematic view showing a biosensor in accordance with a fourth embodiment of the invention. The same elements of the biosensor 4 and the biosensors 1 and 2 are not described here, for simplicity. To improve resonance absorption effects of the end surface of the SPR unit, the biosensor 4 shown in FIG. 4 can be applied. The biosensor 4 is formed with a triangular resonance cavity, wherein two reflective surfaces therein are coated with the SPR units 401. Because the laser is not vertically incident on the reflective surface of the laser on the SPR unit 401, a suitable angle can be chosen to maximize the surface plasmon resonance effects. The optical resonator of the semiconductor layer of the biosensor in the invention can be an optical resonator with multiple reflective surfaces. The semiconductor laser device in this embodiment can be an FP semiconductor layer or a DFB laser.

The semiconductor laser device is operated by injecting carriers to thereby emit the laser. Three basic conditions need to be achieved to operate the semiconductor laser device, including:

(i) Enough population inversion distribution is needed, i.e. the number of atoms in the upper state is larger than that of atoms in the lower state;

(ii) A suitable optical resonator is needed to provide feedback reaction, thereby exciting and increasing the photons and forming laser resonance; and (iii) A threshold value of the injection current must be achieved to make gain of the photon equal to or greater than the consumption of the photon. The semiconductor laser device is formed with an optical resonator and the photon of the stimulated emission in the optical resonator travels back and forth therein for several times and generates more stimulated emission while achieving a state of population inversion, thus obtaining a laser of great coherence and directionality at the output end. Light intensity of the laser outputted by the semiconductor laser device will be affected by the reflectivity of the optical resonator. When a stable current greater than the threshold current is applied to the semiconductor layer, the outputted laser with a relatively stable light intensity will be obtained.

Since the metal film, i.e. the SPR unit, functions as the reflective surface of the optical resonator of the semiconductor laser device and surface plasmon resonance effects occur therein, most of the energy is fully reflected back to the optical resonator while the photon is incident on the SPR unit and a part of the energy is absorbed by the SPR unit in the evanescent wave form. When the bound specific biological molecules on the SPR unit reacts with the sample, i.e., the analyzed object, a variation of the energy of the evanescent wave occurs, whereby the photon energy reflected by the SPR unit is adjusted by a biological reaction signal over the SPR unit, thus resulting in the outputted laser intensity signal to vary with variations of the biological reaction signals. Optical amplification of the biological reaction signals is thus achieved.

Figure 5:
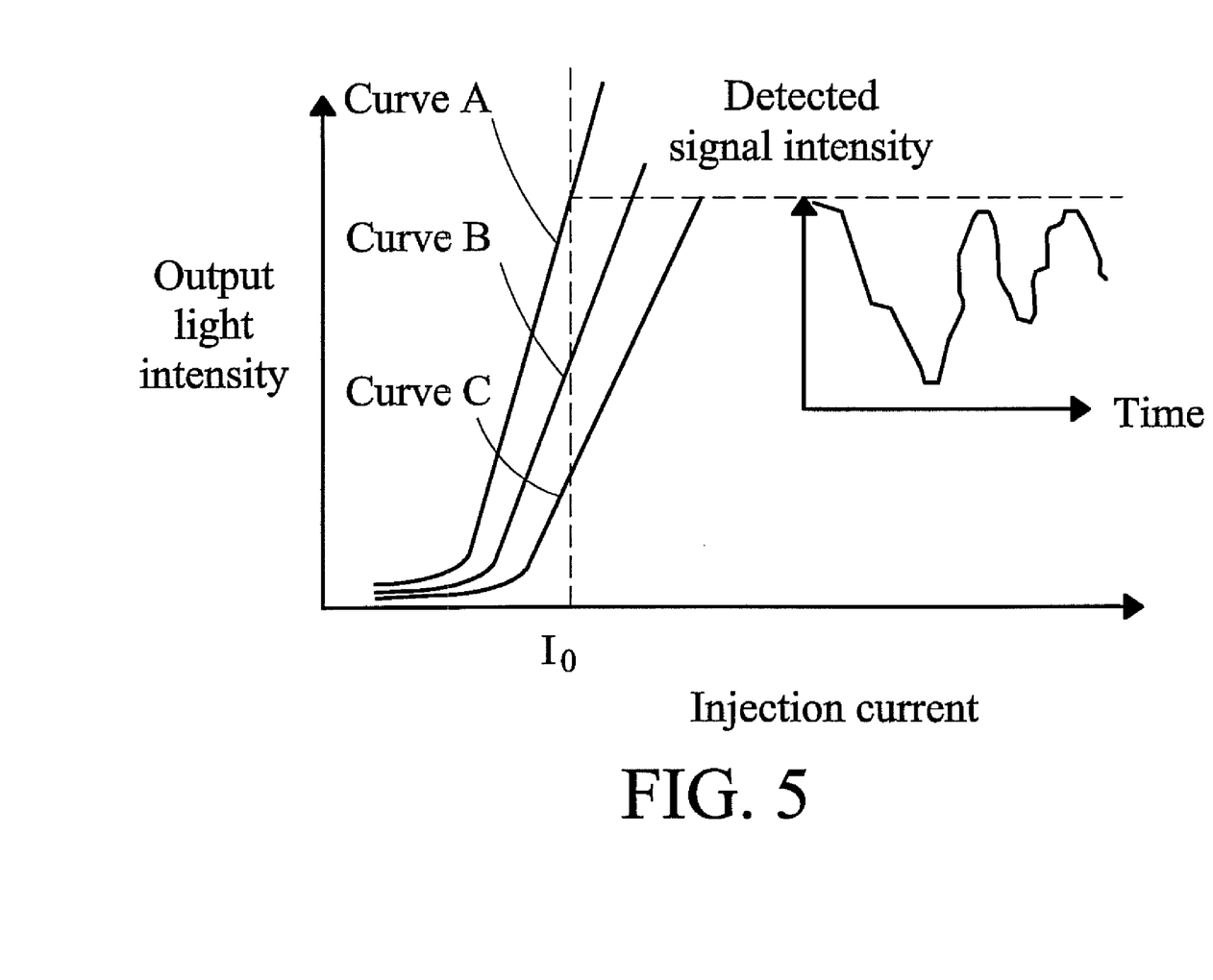
FIG. 5 is a diagram showing biological response signals outputted by a semiconductor laser device of a biosensor of the present invention.

FIG. 5 is a response diagram showing biological response signals outputted by a semiconductor laser device of a biological transmission and detecting device of the invention. As shown in FIG. 5, the curve A represents a response diagram between the outputted light intensity and injection currents while no sample is provided. When various sample solutions are added, the evanescent wave intensity arising from the photon incident on the SPR unit will change and influence the reflectivity of the photon on the SPR unit, thereby correspondingly changing consumption parameters of the laser and resulting in different response curves between the injection current $I_0$ and light output intensities, as illustrated as curves B and C in FIG. 5. In an ideal condition, when the injection current $I_0$ is maintained, the output light intensity of the semiconductor laser device should also be maintained. If the biological response signals cause variation of consumption of the semiconductor laser device, even though the injection current is maintained, the laser output light intensity still changes and the detecting unit can thus detect the signal variation and obtain a curve between the detected signal intensity and time, and then reaction conditions of the sample and the specific biological molecules can thus be analyzed in time.

As described above, the biosensor of the present invention incorporates multiple amplification characteristics of a semiconductor laser device and the photon in the optical resonator is adjusted by surface plasmon resonance of the reflective surface of the optical resonator while traveling back and forth therein. The photon energy is correspondingly adjusted by the biological molecule signal on the surface of the SPR unit. Following multiple photon travels, the biological molecule signal on the surface of the SPR unit will thus be effectively amplified, thereby allowing weak biological reaction signals to be easily detected and thus simplifying the detection method of the biosensor.

As described above, the biosensor with semiconductor laser device has the following three advantages. (1) The semiconductor laser device is formed with a reduced volume and can be formed with high integration. (2) Due to the laser optical amplification theory, the sensitivity of the biosensor can be improved. (3) The biosensor may perform direct amplification of the biological reaction signal and thus reduce signal detection costs, thereby reducing manufacturing costs.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A biosensor comprising:
a semiconductor laser device comprising an optical resonator with at least one reflective surface and a light output surface, wherein the semiconductor laser device comprises:
an active layer,
a P-type carrier confinement layer disposed on a side of the active layer,
an N-type carrier confinement layer disposed on another side of the active layer,
a P-type electrode disposed on the P-type carrier confinement layer, and
an N-type electrode disposed on the N-type carrier confinement layer; and
a surface plasmon resonance (SPR) unit disposed on the at least one reflective surface of the optical resonator.

2. The biosensor as claimed in claim 1, wherein the semiconductor laser device is a Fabry-Perot (FP) semiconductor laser device or a distributed feedback (DFB) laser, and the optical resonator of the FP semiconductor laser device is a Fabry-Perot (FP) cavity.

3. The biosensor as claimed in claim 1, wherein the SPR unit is a dielectric layer, a metal film, a semiconductor layer or a dielectric layer composed of metal oxide, and the metal film comprises Au, Ag, Cu or a composite multi-layer thereof.

4. The biosensor as claimed in claim 1, further comprising a binding layer covering the SPR unit for fixing specific biological molecules to be reacted with corresponding biological molecules of an analyzed object.

5. The biosensor as claimed in claim 4, wherein the specific biological molecules comprise DNA segments, antigen, antibody, enzyme, or co-enzyme.

6. The biosensor as claimed in claim 1, furthering comprising a detecting unit disposed on a direction along an output direction of the semiconductor laser device, wherein the detecting unit comprises a light intensity detecting unit to output detected results in either a current form or a voltage form.

7. The biosensor as claimed in claim 1, wherein the active layer is a P-type GaAs semiconductor layer, the P-type carrier confinement layer is a P-type $Al_xGa_{1-x}As$ semiconductor layer, the N-type carrier confinement layer is an N-type $Al_xGa_{1-x}As$ semiconductor layer, the P-type electrode comprises Ni/Au alloy, and the N-type electrode comprises Ti/Al/Au alloy.

8. The biosensor as claimed in claim 1, wherein at least one cleavage end surface of the active layer is the reflective surface, the other cleavage end surface of the active layer is the light output surface, thereby forming the optical resonator.

9. The biosensor as claimed in claim 8, wherein the active layer further comprises a Bragg grating disposed therein corresponding the reflective surface, thereby forming the optical resonator.

10. The biosensor as claimed in claim 8, wherein the N-type electrode and the P-type electrode are narrow strip structures extending from the reflective surface to the light output surface.

11. The biosensor as claimed in claim 8, further comprising two isolation regions respectively disposed on both sides of the SPR unit and the reflective surface of the semiconductor laser device, thereby preventing the SPR unit from being electrically connected with the N-type electrode and P-type electrode.

12. The biosensor as claimed in claim 11, wherein the isolation regions form a trench for enabling the specific biological molecules to react with corresponding biological molecules of the analyzed object.

13. The biosensor as claimed in claim 11, wherein the isolation regions comprise insulating materials.

14. The biosensor as claimed in claim 1, further comprising a first dielectric layer formed on the light output surface, thereby partially reflecting and transmitting the light and forming a Fabry Perot (FP) semiconductor laser device.

15. The biosensor as claimed in claim 14, wherein the first dielectric layer is formed by alternately stacked dielectric films, and the dielectric film comprises $SiO_2$, $TiO_2$, ZnS or $MgF_2$.

16. The biosensor as claimed in claim 14, further comprising a second dielectric layer disposed on the reflective surface and the SPR unit.

17. The biosensor as claimed in claim 16, wherein the second dielectric layer is formed by alternately stacked dielectric films, and the dielectric film comprises $SiO_2$, $TiO_2$, ZnS or $MgF_2$.

18. The biosensor as claimed in claim 1, wherein the optical resonator of the semiconductor laser device is a triangular resonator structure having two reflective surfaces coated with the SPR unit.

19. The biosensor as claimed in claim 1, wherein the semiconductor layer comprises a plurality of the reflective surfaces coated with the SPR unit.

* * * * *